US011938050B2

(12) United States Patent
Gregg et al.

(10) Patent No.: US 11,938,050 B2
(45) Date of Patent: Mar. 26, 2024

(54) TORQUE CONTROL METHODS AND DEVICES FOR POWERED ORTHOSIS

(71) Applicant: BOARD OF REGENTS, THE UNIVERSITY OF TEXAS SYSTEM, Austin, TX (US)

(72) Inventors: Robert D. Gregg, Allen, TX (US); Ge Lv, Dallas, TX (US); Hanqi Zhu, Dallas, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 214 days.

(21) Appl. No.: 16/061,905

(22) PCT Filed: Dec. 8, 2016

(86) PCT No.: PCT/US2016/065558
§ 371 (c)(1),
(2) Date: Jun. 13, 2018

(87) PCT Pub. No.: WO2017/105996
PCT Pub. Date: Jun. 22, 2017

(65) Prior Publication Data
US 2018/0360639 A1 Dec. 20, 2018

Related U.S. Application Data

(60) Provisional application No. 62/266,959, filed on Dec. 14, 2015.

(51) Int. Cl.
B25J 9/00 (2006.01)
A61F 5/01 (2006.01)
(Continued)

(52) U.S. Cl.
CPC .......... A61F 5/0127 (2013.01); A61F 5/0123 (2013.01); A61H 3/00 (2013.01);
(Continued)

(58) Field of Classification Search
CPC ........ A61H 1/00; A61H 1/001; A61H 1/0266; A61H 3/00
See application file for complete search history.

(56) References Cited

U.S. PATENT DOCUMENTS 7,190,141 B1 * 3/2007 Ashrafiuon ............ B25J 9/0006
318/568.14
9,566,705 B2 * 2/2017 Goldfarb ................... A61F 2/72
(Continued)

FOREIGN PATENT DOCUMENTS

CA 2876187 A1 12/2013

OTHER PUBLICATIONS

Andersson, GBJ et al. "Correlations between changes in gait and in clinical status after knee arthroplasty." Acta Orthopaedica Scandinavica 52.5: 569-573; especially pp. 570-571 (Jul. 8, 2009).
(Continued)

Primary Examiner — Bradley H Philips
Assistant Examiner — Savannah L Gabriel
(74) Attorney, Agent, or Firm — Parker Highlander PLLC

(57) ABSTRACT

Orthosis device and related methods for controlling the device to counteract a gravitational force exerted on the person without directing the orthosis device in a pre-determined pattern of motion.

20 Claims, 10 Drawing Sheets

(51) Int. Cl.
    *A61H 3/00*    (2006.01)
    *B25J 9/16*    (2006.01)
(52) U.S. Cl.
    CPC .......... *B25J 9/0006* (2013.01); *B25J 9/1638*
              (2013.01); *A61F 2005/0155* (2013.01)

(56) References Cited

U.S. PATENT DOCUMENTS

| | | | | |
|---|---|---|---|---|
| 2004/0106881 | A1* | 6/2004 | McBean | A61F 2/72 601/5 |
| 2004/0158175 | A1* | 8/2004 | Ikeuchi | A61H 3/008 601/5 |
| 2005/0070834 | A1* | 3/2005 | Herr | A61F 5/0127 602/28 |
| 2005/0102111 | A1* | 5/2005 | Dariush | B25J 9/0006 702/41 |
| 2006/0173552 | A1* | 8/2006 | Roy | A63B 71/0009 623/24 |
| 2006/0241539 | A1* | 10/2006 | Agrawal | A61H 1/024 602/26 |
| 2006/0270950 | A1* | 11/2006 | Dariush | A61H 3/008 601/5 |
| 2008/0154165 | A1* | 6/2008 | Ashihara | B25J 9/0006 602/23 |
| 2008/0249438 | A1* | 10/2008 | Agrawal | A61H 1/0237 602/23 |
| 2009/0265018 | A1 | 10/2009 | Goldfarb et al. | |
| 2012/0283845 | A1* | 11/2012 | Herr | A61F 2/68 623/24 |
| 2013/0226048 | A1* | 8/2013 | Unluhisarcikli | A61H 1/00 601/34 |
| 2013/0296754 | A1* | 11/2013 | Campbell | A61F 5/3761 602/16 |
| 2014/0142474 | A1* | 5/2014 | McBean | A61F 5/0127 601/33 |
| 2015/0051528 | A1* | 2/2015 | Gilbert | A61F 2/604 602/16 |
| 2015/0142130 | A1* | 5/2015 | Goldfarb | A61H 1/0244 623/25 |
| 2016/0331557 | A1* | 11/2016 | Tong | A61F 2/6607 |

OTHER PUBLICATIONS

Blankentstein, Guido, Romeo Ortega, and Arjan J. Van Der Schaft. "The matching conditions of controlled Lagrangians and IDA-passivity based control." *International Journal of Control* 75.9 (2002): 645-665.

De Leva, Paolo. "Adjustments to Zatsiorsky-Seluyanov's segment inertia parameters." *Journal of Biomechanics* 29.9 (1996): 1223-1230.

Duschau-Wicke, Alexander, et al. "Adaptive support for patient-cooperative gait rehabilitation with the lokomat." *2008 IEEE/RSJ International Conference on Intelligent Robots and Systems*. IEEE, 2008.

Farris, Ryan J., Hugo A. Quintero, and Michael Goldfarb. "Preliminary evaluation of a powered lower limb orthosis to aid walking in paraplegic individuals." *IEEE Transactions on Neural Systems and Rehabilitation Engineering* 19.6 (2011): 652-659.

Gban, Justin, Ryan Steger, and Hami Kazerooni. "Control and system identification for the Berkeley lower extremity exoskeleton (BLEEX)." *Advanced Robotics* 20.9 (2006): 989-1014.

Gregg, Robert D., and Jonathon W. Sensinger. "Biomimetic virtual constraint control of a transfemoral powered prosthetic leg." *2013 American Control Conference*. IEEE, 2013.

Gregg, Robert D., et al. "Virtual constraint control of a powered prosthetic leg: From simulation to experiments with transfemoral amputees." *IEEE Transactions on Robotics* 30.6 (2014): 1455-1471.

Hidler, Joseph, et al. "Multicenter randomized clinical trial evaluating the effectiveness of the Lokomat in subacute stroke." *Neurorehabilitation and Neural Repair* 23.1 (2009): 5-13.

International Preliminary Report on Patentability for PCT/US2016/065558 dated Jun. 28, 2018.

International Search Report + Written Opinion for PCT/US2016/065558 dated Feb. 28, 2017.

Jahns, Thomas M., and Wen L. Soong. "Pulsating torque minimization techniques for permanent magnet AC motor drives—a review." *IEEE Transactions on Industrial Electronics* 43.2 (1996): 321-330.

John, Joseph P., S. Suresh Kumar, and B. Jaya. "Space vector modulation based field oriented control scheme for brushless DC motors." *2011 International Conference on Emerging Trends in Electrical and Computer Technology*. IEEE, 2011.

Lv, Ge, and Robert D. Gregg. "Orthotic body-weight support through underactuated potential energy shaping with contact constraints." *2015 54th IEEE Conference on Decision and Control (CDC)*. IEEE, 2015.

Lv, Ge, and Robert D. Gregg. "Underactuated potential energy shaping with contact constraints: Application to a powered knee-ankle orthosis." *IEEE Transactions on Control Systems Technology* 26.1 (2018): 181-193.

Mace, Michael, et al. "A heterogeneous framework for real-time decoding of bioacoustic signals: Applications to assistive interfaces and prosthesis control." *Expert Systems with Applications* 40.13 (2013): 5049-5060.

Oksuztepe, Eyyup, Zeki Omac, and Hasan Kurum. "Sensorless vector control of PMSM with non-sinusoidal flux using observer based on FEM." *Electrical Engineering* 96.3 (2014): 227-238.

Sankai, Yoshiyuki. "HAL: Hybrid assistive limb based on cybernics." *Robotics Research*. Springer, Berlin, Heidelberg, 2010. 25-34.

Sanz-Merodio, Daniel, et al. "A lower-limb exoskeleton for gait assistance in quadriplegia." *2012 IEEE International Conference on Robotics and Biomimetics (ROBIO)*. IEEE, 2012.

Strausser, Katherine A., and H. Kazerooni. "The development and testing of a human machine interface for a mobile medical exoskeleton." *2011 IEEE/RSJ International Conference on Intelligent Robots and Systems*. IEEE, 2011.

Talaty, Mukul, Alberto Esquenazi, and Jorge E. Briceno. "Differentiating ability in users of the ReWalk TM powered exoskeleton: An analysis of walking kinematics." *2013 IEEE 13th International Conference on Rehabilitation Robotics (ICORR)*. IEEE, 2013.

Tucker, Michael R., et al. "Control strategies for active lower extremity prosthetics and orthotics: a review." *Journal of Neuroengineering and Rehabilitation* 12.1 (2015): 1.

Waters, Robert L., and Sara Mulroy. "The energy expenditure of normal and pathologic gait." *Gait & Posture* 9.3 (1999): 207-231.

Westervelt, Eric R., Jessy W. Grizzle, and Daniel E. Koditschek. "Hybrid zero dynamics of planar biped walkers." *IEEE Transactions on Automatic Control* 48.1 (2003): 42-56.

Yan, Tingfang, et al. "Review of assistive strategies in powered lower-limb orthoses and exoskeletons." *Robotics and Autonomous Systems* 64 (2015): 120-136.

\* cited by examiner

Fig. 6. Schematic of control system, where $\theta_a$ is the ankle angle, $\theta_l$ is the shank angle, $F_1$ and $F_2$ are the ground reaction forces, $T_r$ is the torque reference, $T_f$ is actuator torque output feedback, $I_r$ is current reference, and $I_f$ is motor's active current.

TORQUE CONTROL METHODS AND DEVICES FOR POWERED ORTHOSIS

CROSS-REFERENCE TO RELATED APPLICATIONS

This application is a national phase application under 35 U.S.C. § 371 of International Application No. PCT/US2016/065558, filed Dec. 8, 2016, which claims priority to U.S. Provisional Patent Application Ser. No. 62/266,959 filed Dec. 14, 2015 and entitled "Torque Control Methods for Powered Orthosis", the contents of each of which are incorporated herein by reference.

GOVERNMENT LICENSE RIGHTS

This invention was made with government support under HD080349 by the National Institute of Child Health and Human Development of the NIH. The government has certain rights in the invention.

BACKGROUND INFORMATION

Lower-limb orthoses and exoskeletons have been developed with different structures and control strategies to assist users during their locomotion. Rehabilitation orthoses and exoskeletons are tools that aim to relieve the repetitive and physically tasking duties of the clinicians and therapists as well as improving the patient's recovery efficacy [1]. Traditional control methodologies for rehabilitation exoskeletons are designed to replicate normal kinematics (joint angles/velocities) and thus fall into the category of kinematic control. This approach is especially useful for providing assistance to individuals with spinal cord injury, who cannot contribute to the kinematic patterns of their own legs. Many exoskeletons have adopted this control paradigm to generate missing function for the user's lower limbs, e.g., [2]-[7].Even though these devices have shown promising results, their controllers force patients to follow pre-defined walking patterns, which may not be desirable for patients with some control of their lower limbs, such as stroke patients [8].

An alternative control category, kinetic control, enforces kinetic goals (e.g., torques or energy) instead of kinematic trajectories, which could provide more flexible gait training paradigms. Instead of constraining a person's motion in a pre-defined manner, kinetic control could provide a supportive environment to allow the person to relearn their own personal, preferred gait. However, exoskeletons typically utilize kinematic strategies that compensate for chronic deficits instead of enabling recovery of patient's normative gait [9]. Related to kinetic control, although not designed for physical rehabilitation, the BLEEX enhances the ability of an able-bodied person to carry extra heavy loads, using force control to minimize the user's interaction forces with the exoskeleton so the person does not feel the weight of the backpack [10]. However, minimizing interaction forces with the exoskeleton does not offload the body weight of the human user as needed in rehabilitation. Kinetic control methods that could enable greater flexibility for powered exoskeletons need to be developed for gait rehabilitation systems.

SUMMARY

Exemplary embodiments of the present disclosure comprise a nonlinear control method of potential energy shaping [11] that is well suited for kinetic control of exoskeletons. By altering the potential energy of the human dynamics in the closed loop, bodyweight support (BWS) can be provided virtually through the actuators of powered lower-limb exoskeletons, allowing persons to train their walking motions naturally as well as freeing up therapists to make corrections. However, the changing contact conditions and degrees of underactuation encountered during human walking present significant challenges to consistently matching a desired potential energy for the human in closed loop. Accordingly, contact-invariant ways of matching desired dynamics disclosed herein enable exoskeletal BWS. Beneficial effects of this control methodology are disclosed herein with simulations and experiments of a powered orthosis during human walking [12], [13]. This feedback control strategy is fundamentally task-invariant, and its parameterization allows systematic adjustments for patient-specific therapy.

Conventional techniques provide weight support for patients through a torso or hip harness attached to an overhead lift. However, conventional BWS training systems are stationary (i.e., mounted to a ceiling or above a treadmill) and labor-intensive for clinicians (who must move the full weight of the limbs), which constrains patients' therapies to clinical environments and greatly reduces the efficiency and frequency of training. Although current powered exoskeletons address the challenge of mobility, their control systems follow pre-defined joint patterns to offload bodyweight. These conventional exoskeleton control systems discourage patients from actively participating in the training process and do not allow patients to relearn their own natural walking gait. The proposed devices and control systems virtually provide BWS to reduce the gravitational forces experienced by the patient's center of mass and lower extremities during locomotion without pre-defined patterns, which can allow patients to relearn their natural walking gaits while training outside of clinical environments.

Exemplary embodiments disclosed herein demonstrate validation of the potential energy shaping approach, which can be implemented in a highly backdrivable, torque-controlled powered ankle foot orthosis (PAFO). The orthosis dynamics are modeled with contact constraints corresponding to heel contact, flat foot, toe contact, and no contact (i.e., swing). In addition, energy shaping control laws are derived for the ankle actuator to provide virtual BWS to a human subject. Torque profiles from simulations provide a reference for the PAFO hardware design.

The mechanical and electronic design of the PAFO is demonstrated to validate its closed-loop torque control capabilities for implementing the potential energy shaping controller. Testing with an able-bodied person with this PAFO is also presented, demonstrating the feasibility of the potential energy shaping approach for both positive and negative virtual body-weight augmentation.

Exemplary embodiments of the present disclosure include a method for controlling an orthosis device coupled to a leg of a person. In particular embodiments, the method comprises: measuring forces exerted on the orthosis device, where the orthosis device comprises an actuator, a plurality of support members and a plurality of sensors, and where the forces include a gravitational force exerted on the person; applying a torque to one of the plurality of support members by the actuator; and controlling the torque applied by the actuator, where the torque applied by the actuator is controlled to counteract the gravitational force exerted on the person; and torque applied by the actuator is not controlled to direct the orthosis device in a pre-determined pattern of motion.

In certain embodiments, the torque applied by the actuator is controlled by a closed-loop potential energy shaping control system. In particular embodiments, the torque applied by the actuator is kinetically controlled via a nonlinear control method. In some embodiments, controlling the torque to the actuator comprises varying the current to an electric motor. In specific embodiments, the electric motor is a permanent magnetic synchronous motor.

In certain embodiments, the orthosis device comprises a first support member placed under a foot of the person; the orthoses device comprises a second support member coupled to a shin of the person; and the actuator is configured to vary the angle between the first support member and the second support member. In particular embodiments, the orthoses device comprises a third support member coupled to the thigh of a user, and a second actuator configured to vary the angle between the third support member and the second support member. In some embodiments, measuring forces exerted on the orthosis device with a plurality of sensors comprises measuring a force in a ball area of the foot of the person via a first sensor in the first support member. In specific embodiments, measuring forces exerted on the orthosis device with a plurality of sensors comprises measuring a force in a heel area of the foot of the person via a second sensor in the first support member.

In certain embodiments, the actuator comprises an electric motor coupled to a gearbox and a first sprocket; the orthosis device comprises a second sprocket coupled to the first support member; and the orthosis device comprises a belt coupling the first sprocket and the second sprocket. Particular embodiments, further comprise measuring the torque applied to one of the plurality of support members by the actuator with a reaction torque sensor.

In some embodiments, the gearbox comprises a planetary gear transmission, and the reaction torque sensor measures the torque at an end of the planetary gear transmission. Specific embodiments further comprise measuring an angle of the second support member via an inertial measurement unit.

Certain embodiments include an orthosis device comprising: a first support member; a second support member; a plurality of sensors configured to measure forces exerted on the orthosis device, wherein the forces exerted on the orthosis device include a gravitational force; an actuator configured to apply a torque to the first or second support member; and a controller configured to control the torque applied by the actuator, wherein the torque is controlled to counteract the gravitational force exerted on the person and device and wherein the torque is not controlled to direct the orthosis device in a pre-determined pattern of motion. In particular embodiments, the controller comprises a closed-loop potential energy shaping control system. In some embodiments, the torque applied by the actuator is kinetically controlled via a nonlinear control method. In specific embodiments, the actuator comprises an electric motor, and wherein the controller is configured vary the current to the electric motor.

In certain embodiments, the first support member is configured to be placed under a foot of a person; the second support member is configured to be coupled to a shin of a person; and the actuator is configured to vary the angle between the first support member and the second support member. In particular embodiments, the plurality of sensors comprises a first sensor in the first support member configured to measure a force in a ball area of the foot of the person. Certain embodiments include a third support member configured to be coupled to the thigh of a person, and a second actuator configured to vary the angle betweent the third and second support members. In some embodiments, the plurality of sensors comprises a second sensor in the first support member configured to measure a force in a heel area of the foot of the person. Specific embodiments further comprise an inertial measurement unit configured to measure an angle of the second support member.

Certain embodiments further comprise an optical encoder configured to measure an angle between the first support member and the second support member. In particular embodiments, the actuator comprises an electric motor coupled to a gearbox and a first sprocket; the orthosis device comprises a second sprocket coupled to the first support member; and the orthosis device comprises a belt coupling the first sprocket and the second sprocket. Some embodiments further comprise a reaction torque sensor coupled to the gearbox. In specific embodiments, the gearbox comprises a planetary gear transmission, and wherein the reaction torque sensor is configured to measure torque at an end of the planetary gear transmission.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
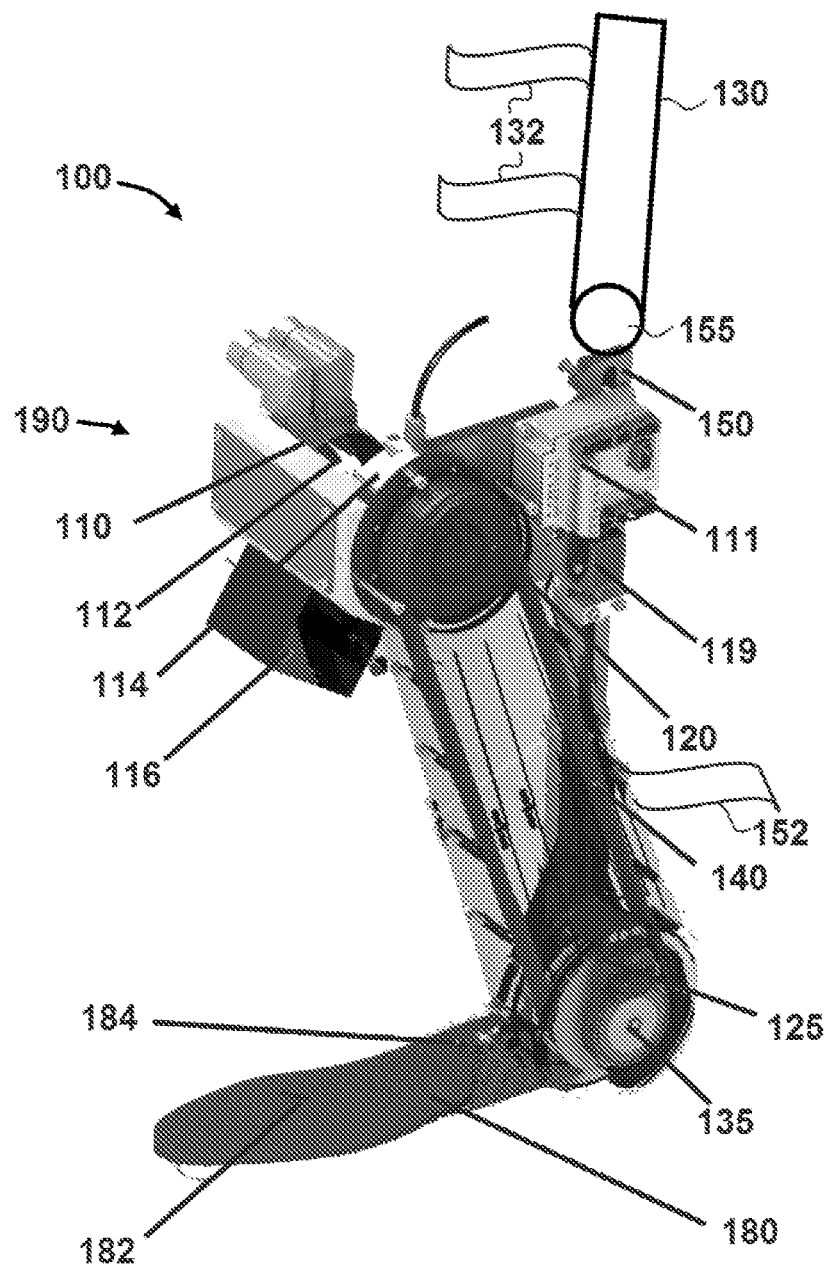
FIG. 1 illustrates a schematic view of a device according to exemplary embodiments of the present disclosure.

Referring now to FIG. 1, an orthosis (also referred to herein as an orthopedic or orthosis device) 100 is configured as a powered ankle-foot orthosis (PAFO). An overview of device 100 will be presented initially, followed by a more detailed description of the device and its operation. It is understood that device 100 shown in FIG. 1 is merely an exemplary embodiment, and that other embodiments may comprise different components or a different configuration of components, including for example, powered knee-ankle orthosis, powered hip-knee-ankle orthosis, and bilateral powered hip-knee-ankle exoskeleton (i.e., both legs).

The embodiment shown in FIG. 1 comprises an actuator 190, an upper support member 130, and an intermediate support 150 member coupled to a lower support member 180. In this embodiment, upper support member 130 may be coupled to a user's thigh area via straps 132, while intermediate support member 150 can be coupled to a user's shin area via straps 152. Upper support member 130 and intermediate support member 150 can be coupled via a pivoting joint 155, and lower support member 180 can be coupled to a user's foot (e.g. proximal to an insole in the user's shoe). In this embodiment actuator 190 comprises a motor 110 coupled to a gearbox 112.

In the embodiment shown in FIG. 1, motor 110 and gearbox 112 are also coupled to a driver sprocket 120 and a driven sprocket 125 via a belt 140. In certain embodiments, belt 140 may be configured as a timing belt or a chain or any flexible member configured to transfer relative rotational motion from driver sprocket 120 to driven sprocket 125.

In addition, motor 110 is coupled to a torque sensor 114 and torque sensor amplifier 116. Device 100 further comprises a motor controller 111 and an inertial measurement unit 119. In the embodiment of FIG. 1, device 100 also comprises a ball force sensor 182 and a heel sensor 184 coupled to lower support 180 as well as an encoder 135 coupled to driven sprocket 125.

In a particular embodiment, motor 110 may be configured as a permanent magnetic synchronous motor (PMSM) and gearbox 112 may be configured as a two stage planetary gear transmission (e.g. TPM 004X-031x-1x01-053B-W1-999, Wittenstein, Inc.). In specific embodiments, belt 140 may also be configured as a poly chain GT Carbon timing belt (e.g. 8MGT 720, Gates Industry, Inc.). Such a configuration can provide the desired torque outputs and can be used to move the actuator's weight closer to the user's center of mass, which can minimize the metabolic burden of the added weight [19].

In certain embodiments of device 100 with an overall transmission ratio of 43.71:1, an efficiency of 0.9, and a motor peak torque of 1.29 Nm, the maximum output torque that actuator 190 can achieve is 50 Nm. In addition, actuator 190 can provide 288 W peak power, which should be sufficient for normal human walking speed under the control algorithm disclosed herein. The combination of a high torque PMSM with a low ratio transmission can minimize backdrive torque and provide comfort to the user.

To achieve accurate torque control performance, motor 110 can be configured as a PMSM with distributed winding, which has sinusoidal back-EMF [20]. Such a configuration can be utilized to reduce the torque ripple and to produce smoother torque output. In a particular embodiment, controller 111 may be configured as a field oriented motor controller (e.g. GSol-Gut-35/100, Elmo Motion Control, Inc.). Such a configuration has a lower response time and torque ripple compared to trapezoidal motor control [21]. In certain embodiments, Hall sensors and a resolver can be coupled to motor 110 to obtain accurate position feedback for controller 111.

Given the requirements of the proposed algorithm, the user's gait phase, ankle angle, and absolute shank angle can be measured by force sensors 182 and 184 (e.g. FlexiForce A301, Tekscan, Inc.), encoder 135, and inertial measurement unit 119. Sensors 182 and 184 can be embedded into lower support member 180 which can be configured as an insole which is placed beneath the user's foot for detecting the phase of gait, e.g., stance vs. swing. In exemplary embodiments, force sensors 182 and 184 can be placed within the normal COP trajectory to provide precise readings, where force sensor 182 can be placed under the ball of the foot, while force sensor 184 can be placed under the heel.

In certain embodiments, lower support member 180 can be produced on a Connex 350 3D printer and made from a rubber-like polyjet photopolymer. In a particular embodiment, encoder 135 is configured as an optical incremental encoder (e.g., 2048 CPR, E6-2048-250-IE-S-H-D-3, US Digital, Inc.), which can be used to obtain the ankle angle. In addition, IMU 119 may be configured as model number 3DM-GX4-25-RS232-SK1, LORD MicroStrain, Inc. and installed on intermediate support member 150 to obtain the absolute shank angle (e.g. the absolute angle of intermediate support member 150. Particular embodiments may include a safety button that must be held continuously by the user to power device 100, i.e., an enable signal. The user could release the button to disable the device 100 at any point during use, e.g., if balance was the lost.

In the embodiment shown, torque sensor 114 is configured as a reaction torque sensor (e.g., TPM 004+, Wittenstein, Inc.) located between a casing for actuator 190 and intermediate support member 150 to measure the real torque output from actuator 190. Information from torque sensor 114 can be used to reduce the actuator torque error caused by the nonlinear transmission efficiency, the variable motor torque constant, and the backdrive torque.

As disclosed herein, exemplary embodiments of device 100 comprise a control system that provides bodyweight support (BWS) for a user. The use of device 100 can prove beneficial for people who have retained partial control of their motor skills, including for example those who have sustained a stroke and other neurological injury. Persons using device 100 are provided with BWS during conventional gait retraining to help them produce the coordinated muscle activities needed for walking. Device 100 can also be used to augment the performance of able-bodied users, e.g., offloading the weight of the user's body or backpack to minimize metabolic burden in soldiers.

Figure 5:
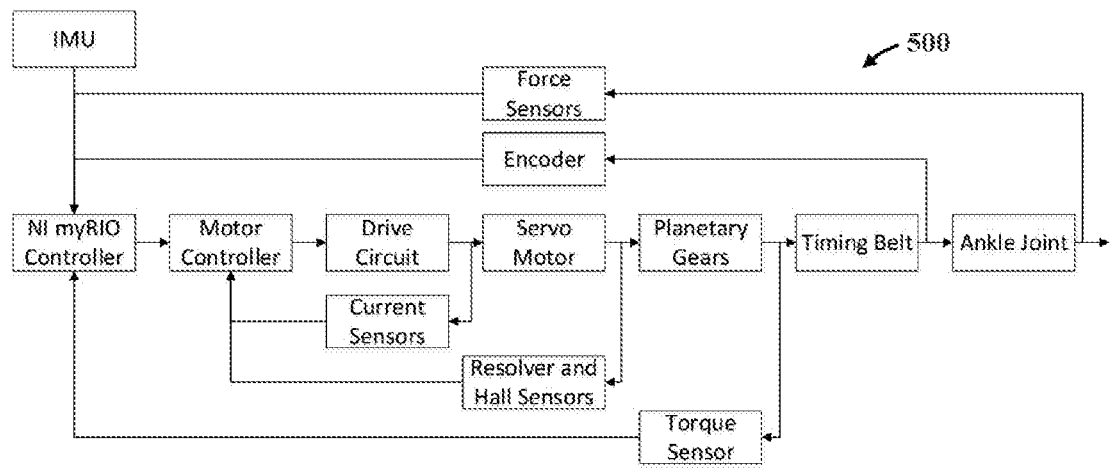
FIG. 5 illustrates a schematic of a hardware system of the embodiment of FIG. 1.

Installing torque sensor 114 at the end of gearbox 112, instead of at the end of the belt 140, avoids additional mass at the ankle joint. By measuring the torque on the case of actuator 190, instead of the output shaft, a non-contact torque sensor can be avoided. This is beneficial since noncontact torque sensors are usually more expensive, larger in size, and heavier than the adopted reaction torque sensor. The system schematic is shown in FIG. 5.

Figure 6:
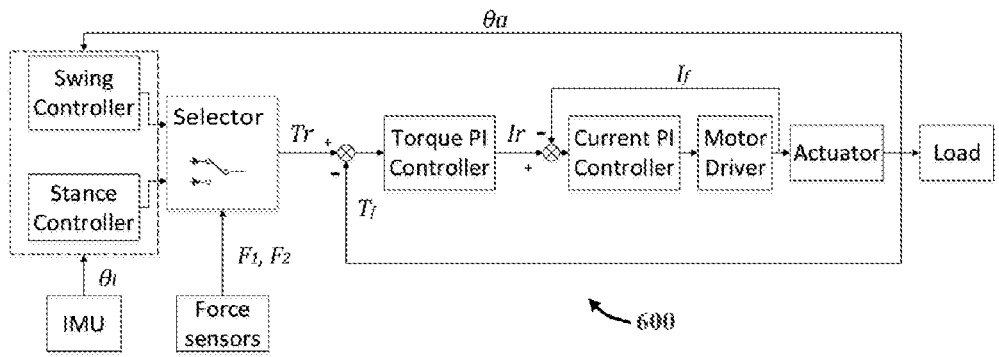
FIG. 6 illustrates a schematic of a control system of the embodiment of FIG. 1.

In order to provide accurate torque tracking, a torque control system was built with two closed loops as shown in the schematic of FIG. 6. As shown in FIG. 6, $\theta_a$ is the ankle angle, $\theta_l$ is the angle of intermediate support member 150 (e.g. shank angle), $F_1$ and $F_2$ are ground reaction forces, $T_r$ is the torque reference, $T_f$ is actuator torque output feedback, $I_r$ is current reference, and $I_f$ is motor's active current. The inner loop is a motor current loop that produces electromagnetic torque Te based on the input active current as $$T_e = (3P/2) \cdot \lambda_m \cdot i_q, \tag{23}$$

where P is the number of motor poles, $\lambda_m$ an is the motor flux linkage, and $i_q$ is the active current in the d-q rotating reference frame [22].

One common methodology to realize torque control is by estimating the active current feedback, transmission ratio, and efficiency of the actuator. However, due to the nonlinear relationship between the motor winding current and the actuator output torque, an outer closed torque control loop was designed to eliminate the torque error. This torque controller tracked the reference torque commanded by the high-level control algorithm, i.e., the stance or swing controller, depending on the contact condition determined by the force sensors. In certain embodiments, controller 111 can be configured as a real time micro-controller (e.g. myRIO-1900, National Instrument, Inc. with a dual-core ARM microprocessor and a Xilinx FPGA) to implement the control algorithms.

Modeling Dynamics

Figure 2:
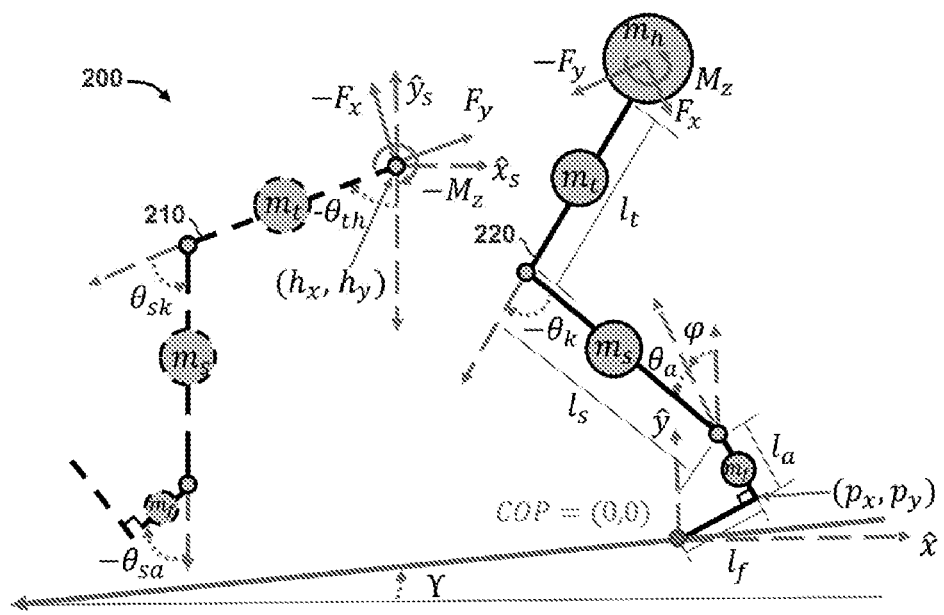
FIG. 2 illustrates a schematic of kinematic model of lower limbs of a person utilized to develop a control scheme for the embodiment of FIG. 1.

Exemplary embodiments of device 100 can be controlled using only feedback local to the leg of a person using device 100. As shown in FIG. 2, kinematic model 200 separately model the dynamics of the stance leg 210 and swing leg 220, which are coupled through interaction forces. For simplicity, it is assumed the masses $m_i$, $i \in \{f, s\}$ are the combined masses of the human limb and its orthosis.

Stance Leg Dynamics

The stance leg is modeled as a kinematic chain with respect to an inertial reference frame (IRF) defined at either the heel or toe, depending on the phase of the stance period (to be discussed later). The configuration of this leg is given by $q_{st}=(p_x, p_y, \phi, \theta_a, \theta_k)^T$, where $p_x$ and $p_y$ are the Cartesian coordinates of the heel, $\Phi$ is the angle of the heel defined with respect to the vertical axis, and $\theta_a$ and $\theta_k$ are the angles of the ankle and knee, respectively. The Lagrangian dynamics can be derived in the form $$M_{st}(q_{st})\ddot{q}_{st}+C_{st}(q_{st},\dot{q}_{st})\dot{q}_{st}+N_{st}(q_{st})+A_l(q_{st})^T\lambda=B_{st}u_{st}+ \\ B_h v_{st}+J_{st}(q_{st})^T F, \tag{1}$$

where $M_{st}$ is the inertia/mass matrix, $C_{st}$ is the Coriolis/centrifugal matrix, $N_{st}$ is the gravitational forces vector. $A_l \in \mathbb{R}^{c \times 5}$ is the constraint matrix defined as the gradient of the constraint functions, c is the number of contact constraints that may change during different contact conditions, and $l \in \{heel, flat, toe\}$ indicates the contact configuration. The Lagrange multiplier $\lambda$ is calculated using the method in [14]. Assuming the orthosis has actuation at the ankle joint, i.e., $u_{st}$, the matrix $B_{st}=(0_{1\times 3}, 1, 0)^T$ maps orthosis torque into the coordinate system. The interaction forces $F=(F_x, F_y, M_z)^T \in \mathbb{R}^{3\times 1}$ between the hip of stance model and the swing thigh are composed of 3 parts: two linear forces and a moment in the sagittal plane [14]. Force vector F is mapped into the system's dynamics by the body Jacobian matrix $J_{st}(q_{st}) \in \mathbb{R}^{3 \times 5}$. The human input term $v_{st}=[v_{ha}, v_{hk}]^T \in \mathbb{R}^{2 \times 1}$ provides torques at the ankle and knee joints, i.e., $v_{ha}$ and $V_{hk}$, which are mapped into the dynamical system through $B_h=(0_{2\times 3}, I_{2\times 2})^T \mathbb{R}^{5\times 2}$. While designing the energy shaping controller, we make no assumptions about the human inputs or interaction forces.

Figure 3:
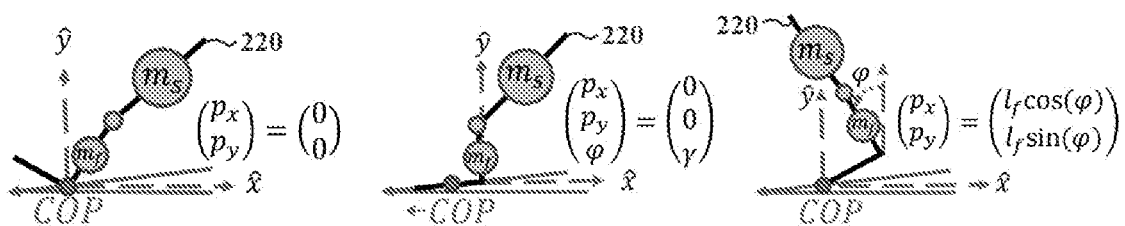
FIG. 3 illustrates a portion of the kinematic model of FIG. 2 in different positions.

During stance phase, the locomotion of the stance leg can be separated into three sub-phases: heel contact, flat foot, and toe contact, as depicted in FIG. 3, for which holonomic contact constraints can be appropriately defined.

(1) Heel Contact: The heel is fixed to the ground as the only contact point, about which the stance leg rotates. The IRF is defined at the heel, yielding the constraint $a_{heel}(q)=0$ and the constraint matrix $A_{heel}=\Delta_q a_{heel}$, where $$a_{heel}:=(p_x,p_y)^T \Rightarrow A_{heel}=(I_{2\times 2}, 0_{2\times 3}). \tag{2}$$

(2) Flat Foot: At this configuration, the foot is flat on the ground slope, where $\phi$ is equal to the slope angle. The IRF is still defined at the heel, which yields the constraint $a_{flat}(q)=0$ and the constraint matrix $A_{flat}=\Delta_q a_{flat}$, where $$a_{flat}:=(p_x,p_y,\phi-\gamma)^T \Rightarrow A_{flat}=(I_{3\times 3}, 0_{3\times 2}) \tag{3}$$

(3) Toe Contact: The toe contact condition begins when the Center of Pressure (COP), the point along the foot where the ground reaction force is imparted, reaches the toe. During this phase the toe is the only contact point, about which the stance leg rotates. The IRF is defined at this contact point to simplify the contact constraints. The coordinates of the heel are then defined with respect to the toe, yielding the constraint $a_{toe}(q)=0$ and the constraint matrix $A_{toe}=\Delta_q a_{toe}$:

$$a_{toe} := (p_x - l_f \cos(\phi), p_y - l_f \sin(\phi))^T, \tag{4}$$

$$\Rightarrow A_{toe} = \begin{pmatrix} 1 & 0 & l_f \sin(\phi) & 0 & 0 \\ 0 & 1 & -l_f \cos(\phi) & 0 & 0 \end{pmatrix}.$$

Swing Leg Dynamics

We choose the hip as a floating base for the swing leg's kinematic chain in FIG. 2. The full configuration of this leg is given as $q_{sw}=(h_x, h_y, \theta_{th}, \theta_{sk}, \theta_{sa})^T$, where $h_x$ and $h_y$ are the positions of the hip, $\theta_{th}$ is the absolute angle defined between the vertical axis and the swing thigh, and $\theta_{sk}$ and $\theta_{sa}$ are the angles of the swing knee and ankle, respectively.

By deriving the equations of motion, we obtain $$M_{sw}(q_{sw})\ddot{q}_{sw}+C_{sw}(q_{sw},\dot{q}_{sw})\dot{q}_{sw}+N_{sw}(q_{sw})=B_{sw}u_{sw}+ \\ B_h v_{sw}-J_{sw}(q_{sw})^T F, \tag{5}$$

where $M_{sw}$ is the inertia/mass matrix, $C_{sw}$ is the Coriolis/centrifugal matrix, $N_{sw}$ is the gravitational forces vector. The matrix $B_{sw}=(0_{1\times 4}, 1)^T$ maps the orthosis torque $u_{sw}$ into the system. The vector F contains the interaction forces between the swing leg and hip (including human hip torques), and $J_{sw}(q_{sw}) \in \mathbb{R}^{3 \times 5}$ maps F into the dynamics. The human input vector $v_{sw}=[v_{sk}; v_{sa}]^T \in \mathbb{R}^{2 \times 1}$ contains human knee and ankle torques $v_{sk}$ and $v_{sa}$, respectively, which are mapped into the coordinate system through $B_h$. There are no contact constraints during swing, i.e., $A_{sw}=0$.

Potential Energy Shaping Control

Equivalent Constrained Dynamics

In this section the equations of motion will be expressed as equivalent constrained dynamics in order to derive an underactuated control law that achieves the desired potential energy for a given contact condition [12], [13]. For the sake of generality the subscripts associated with specific contact conditions will be dropped. To begin, one can calculate the Lagrange multiplier λ, based on the results in [14], [15] as $$\lambda = \hat{\lambda} + \bar{\lambda}u + \overline{\lambda}F;$$

$$\hat{\lambda} = W(\dot{A}\dot{q} - AM^{-1}(C\dot{q}+N-B_h v)),$$

$$\bar{\lambda} = WAM^{-1}B,$$

$$\overline{\lambda} = WAM^{-1}J^T,$$

$$W = (AM^{-1}A^T)^{-1}. \quad (6)$$

Plugging in λ and A, dynamics (1) become:

$$M_\lambda \ddot{q} + C_\lambda \dot{q} + N_\lambda = B_\lambda u + B_{h\lambda}v + J_\lambda^T F, \quad (7)$$

where $$M_\lambda = M,$$

$$C_\lambda = [I - A^T W A M^{-1}]C + A^T W \dot{A},$$

$$N_\lambda = [I - A^T W A M^{-1}]N,$$

$$B_\lambda = [I - A^T W A M^{-1}]B,$$

$$B_{h\lambda} = [I - A^T W A M^{-1}]B_h,$$

$$J_\lambda = J[I - A^T W A M^{-1}]^T. \quad (8)$$

Given (7), the desired form of the equivalent constrained dynamics is given as $$M_\lambda \ddot{q} + C_\lambda \dot{q} + \tilde{N}_\lambda = B_{h\lambda} v + J_\lambda^T F. \quad (9)$$

where $$\tilde{N}_\lambda = [I - A^T W A M]^{-1}\tilde{N}, \quad (10)$$

given the desired gravitational forces vector $\tilde{N}$ that will be introduced later for each configuration. Based on the results in [12] and [13], the desired dynamics (9) can be achieved in closed loop if the following thatching condition is satisfied:

$$B_\lambda^\perp (N_\lambda - \tilde{N}_\lambda) = 0. \quad (11)$$

The underactuated potential shaping control law is then $$u = (B_\lambda^T B_\lambda)^{-1} B_\lambda^T (N_\lambda - \tilde{N}_\lambda). \quad (12)$$

During swing, we have $A_{sw}=0$, hence (11) and 12) reduce to the classical matching condition and control law in [11].

We choose $\tilde{N}_{st}$ in (10) by replacing the gravitational constant in $N_{st}$ with $\tilde{g}<g$ for BWS and $\tilde{g}>g$ for reverse BWS. The upper body segments are lumped into a single point mass at the hip in the stance dynamics. Assuming the stance knee is rigid enough to provide a lever arm from the ankle to the hip, ankle torques will directly map to forces along the stance leg, which can be used to shape the weight of that leg. We approximate a rigid stance knee by setting its angle to zero, i.e., $\theta_k=0$, in the potential energy before deriving, the gravitational forces vector $N_{st}$ that is used to evaluate the matching condition (11) and calculate the control law (12). As a consequence, the row corresponding to this DOF in $N_{st}$ vanishes. We now prove for each contact condition that the weights of the stance shank, thigh, and hip links can be shaped by the orthosis ankle actuator.

1) Heel Contact: We decompose $M_{st}$ into the submatrices $M_1 \in \mathbb{R}^{2 \times 2}$, $M_2 \in \mathbb{R}^{2 \times 3}$, $M_3 \in \mathbb{R}^{3 \times 2}$, and $M_4 \in \mathbb{R}^{3 \times 3}$, to simplify the multiplication between $A_{heel}$ and $M_{st}^{-1}$ with blockwise inversion. Following the derivation in [12], [13]:

$$B_{\lambda 1} = \begin{bmatrix} V_1 B_{st(3,5)} \\ B_{st(3,5)} \end{bmatrix} = \begin{bmatrix} V_{12}P \\ 0 \\ P \end{bmatrix}, \quad (13)$$

$$N_{\lambda 1} = \begin{bmatrix} V_1 N_{st(3,5)} \\ N_{st(3,5)} \end{bmatrix} = \begin{bmatrix} V_{11}N_{st(3,3)} + V_{12}N_{st(4,5)} \\ N_{st(3,3)} \\ N_{st(4,5)} \end{bmatrix},$$

where $V_1=[V_{11}, V_{12}]=M_2 M_4^{-1}$, $V_{11} \in \mathbb{R}^{2 \times 1}$, $V_{12} \in \mathbb{R}^{2 \times 2}$ and $P=[1,0]^T$. The subscript (k, z) indicates rows k through z of a matrix.

Let $\tilde{N}_{\lambda 1}$ be the desired (constrained) gravitational forces vector defined by (10). We choose the annihilator of $B_{\lambda 1}$ as $$B_{\lambda 1}^\perp = \begin{bmatrix} I_{2\times 2} & 0_{2\times 1} & -V_{12} \\ 0_{1\times 2} & 1 & 0_{1\times 2} \\ 0_{1\times 2} & 0 & P^\perp \end{bmatrix}. \quad (14)$$

where $P^\perp=[0, 1]$ is used as an annihilator for P. Plugging terms into (11), the matching condition holds if $\tilde{N}_{st(3,3)}=N_{st(3,3)}$, not shaping the heel orientation DOF. Therefore the control law $u_{heel}$ is defined by (12) after satisfying the matching condition with this assumption.

2) Flat Foot: At this configuration let $M_1 \in \mathbb{R}^{3 \times 3}$, $M_2 \in \mathbb{R}^{3 \times 2}$, $M_3 \in \mathbb{R}^{2 \times 3}$, $M_4 \in \mathbb{R}^{2 \times 2}$. The same procedure yields $$B_{\lambda 2} = \begin{bmatrix} V_2 P \\ P \end{bmatrix}, N_{\lambda 2} = \begin{bmatrix} N_2 N_{st(4,5)} \\ N_{st(4,5)} \end{bmatrix}. \quad (15)$$

where $V_2 = M_2 M_4^{-1} \in \mathbb{R}^{3 \times 2}$. The exact flat-foot control law $u_{flat}$ is given by (12) after satisfying (11) with the annihilator $$B_{\lambda 2}^\perp = \begin{bmatrix} I_{3\times 3} & -V_2 \\ 0_{1\times 3} & P^\perp \end{bmatrix}. \quad (16)$$

3) Toe Contact: At the toe contact configuration we decompose $M_{st}$ as in the Flat Foot case to simplify the derivation. With the same procedure we obtain $$B_{\lambda 3} = \begin{bmatrix} V_4 P \\ P \end{bmatrix}, N_{\lambda 3} = \begin{bmatrix} V_3 N_{st(1,3)} + V_4 N_{st(4,5)} \\ N_{st(4,5)} \end{bmatrix}, \quad (17)$$

where $V_3$ and $V_4$ are defined as $$V_3 = I_{3\times 3} - K, \quad V_4 = KM_2 M_4^{-1},$$
$$K = r^T(r\Delta^{-1}r^T)^{-1}r\Delta^{-1},$$
$$r = \begin{pmatrix} 1 & 0 & l_f \sin(\phi) \\ 0 & 1 & -l_f \cos(\phi) \end{pmatrix}.$$

We choose the annihilator of $B_{\lambda 3}$ as $$B_{\lambda 3}^{\perp} = \begin{bmatrix} I_{3\times 3} & -V_4 \\ 0_{1\times 3} & P^{\perp} \end{bmatrix}. \quad (18)$$

Plugging in (17) and (18), the left-hand side of (11) is $$B_{\lambda 3}^{\perp}(N_{\lambda 3} - \tilde{N}_{\lambda 3}) = V_3(N_{st(1,3)} - \tilde{N}_{st(1,3)}). \quad (19)$$

The matching condition is not satisfied unless we assume $\tilde{N}_{st(1,3)} = N_{st(1,3)}$, i.e., not shaping the unactuated DOF $\phi$ (recall that $p_x$ and $p_y$ are constrained). The toe-contact controller $u_{toe}$ is then defined by (12) under this assumption.

Matching Condition for Swing

For the swing leg, there are no contact constraints defined in the dynamics so the matching condition simplifies. We replace g with $\tilde{g}$ in $N_{sw}$ to define the desired gravitational forces vector $\tilde{N}_{sw}$. Letting $B_{sw}^{\perp} = [I_{4\times 4}, 0_{4\times 1}]$, we have $B_{sw}^{\perp} B_{sw} = 0$ rank $(B_{sw}^{\perp}) = 4$. The loft-band side of the matching condition (11) with A=0 is $$B_{sw}^{\perp}(N_{sw} - \tilde{N}_{sw}) = (N_{sw(1,4)} - \tilde{N}_{sw(1,4)}),$$

The matching condition can be satisfied if first four rows of $N_{sw}$, which correspond to unactuated DOFs, are unshaped: $\tilde{N}_{sw(1,4)} = N_{sw(1,4)}$. Only links distal to the swing actuator can be shaped, i.e., the foot mass. This could assist individuals with weakened dorsiflexors (i.e., drop foot), Given $A_{sw} = 0$, the swing controller reduces from (12) to $$u_{sw} = (B_{sw}^T B_{sw})^{-1} B_{sw}^T (N_{sw} - \tilde{N}_{sw}), \quad (20)$$

where $\tilde{N}_{sw} = [N_{sw(1,4)}^T, \tilde{N}_{sw(5)}^T]^T$.

Passive Walking Model

In order to understand the torques required for the potential energy shaping strategy, we simulate it on humanlike biped model, i.e., combining the stance and swing legs together in FIG. 2. The full biped models configuration space is given as $q_c = (q_{st}^T, \theta_h, \theta_{sk}, \theta_{sa})^T$, where the hip angle $\theta_h$ is defined between the stance and swing thighs. For simplicity we assume symmetry in the full biped, i.e., identical orthoses on both human legs [14]. We adopt the same impedance control paradigm used in [12] and [13] for the human inputs to generate a human-like walking gait, on which we test the orthosis controller. The total input torque vector for the full biped model, including orthotic and human inputs, is $$T = (B_{sw}^T, 0_{1\times 3})^T u_{lf} + (0_{1\times 3}, B_{sw}^T)^T u_{sw} + v_h,$$

$$v_h = [0_{1\times 3}, v_{ha}, v_{hk}, v_{hh}, v_{hsk}, v_{hsa}]^T \in \mathbb{R}^{8\times 1}, \quad (21)$$

where $l \in \{heel, flat, toe\}$ indicates the stance controller based on the contact condition, and $v_h$ is the vector of human inputs. The human torque for a single joint in $v_h$ is given by $$v_{hj} = -K_{pj}(\theta_j - \theta_j^{eq}) - K_{dj}\dot{\theta}_j, \quad (22)$$

where $K_{pj}$, $K_{dj}$, $\theta_j^{eq}$ respectively correspond to the stiffness, viscosity, and equilibrium angle of joint $j \in \{a, k, h, sk, sa\}$.

Biped locomotion is modeled as a hybrid dynamical system which includes continuous and discrete dynamics. Impacts happen when the swing heel contacts the ground and when contact constraints change between the heel contact and flat foot configurations. Note that no impact occurs when switching between the flat foot and toe contact configurations, but the location of the IRF does change from heel to toe. Based on [16], the hybrid dynamics and impact maps during one step are computed in the following sequence:

| | | |
|---|---|---|
| 1. $M_e \ddot{q}_e + Q_e + A_{e_{heel}}^T \lambda_e = \tau$ | if | $a_{e_{flat}} \neq 0$, |
| 2. $\dot{q}_e^+ = (I - X(A_{e_{flat}} X)^{-1} A_{e_{flat}}) \dot{q}_e^-$ | if | $a_{e_{flat}} = 0$, |
| 3. $M_e \ddot{q}_e + Q_e + A_{e_{flat}}^T \lambda_e = \tau$ | if | $|c_p(q, \dot{q})| < l_f$, |
| 4. $\dot{q}_e^+ = \dot{q}_e^-, (q_e(1)^+, q_e(2)^+)^T = g$ | if | $|c_p(q, \dot{q})| = l_f$, |
| 5. $M_e \ddot{q}_e + Q_e + A_{e_{toe}}^T \lambda_e = \tau$ | if | $h(q_e) \neq 0$, |
| 6. $(q_e^+, \dot{q}_e^+) = \Theta(q_e^-, \dot{q}_e^-)$ | if | $h(q_e) = 0$, | where the subscript e indicates the dynamics of the full biped model, $X = M_e^{-1} A_{e_{flat}}^T$, and $g = (l_f \cos(\gamma), l_f \sin(\gamma))^T$ models the change in IRF. The vector $c_p(q, \dot{q})$ is the COP defined with respect to the heel IRF calculated using the conservation law of momentum. The vector $Q_e$ groups the Coriolis/centrifugal terms and gravitational forces for brevity. We denote the ground clearance and ground strike impact map of the swing heel as $h(q_e)$ and $\Theta$, respectively, based on [17]. The aforementioned sequence of continuous and discrete dynamics repeats after a complete step, phase 6 switches back to phase 1 for the next step.

Simulation Results

Average values from adult males [18] were chosen for the model parameters as in [12], [13] with trunk masses grouped at the hip. Following the same procedure presented in [12], the investigators first tuned the human impedance controller's gains to find a stable gait and then implemented the energy shaping control laws disclosed herein.

Figure 4:
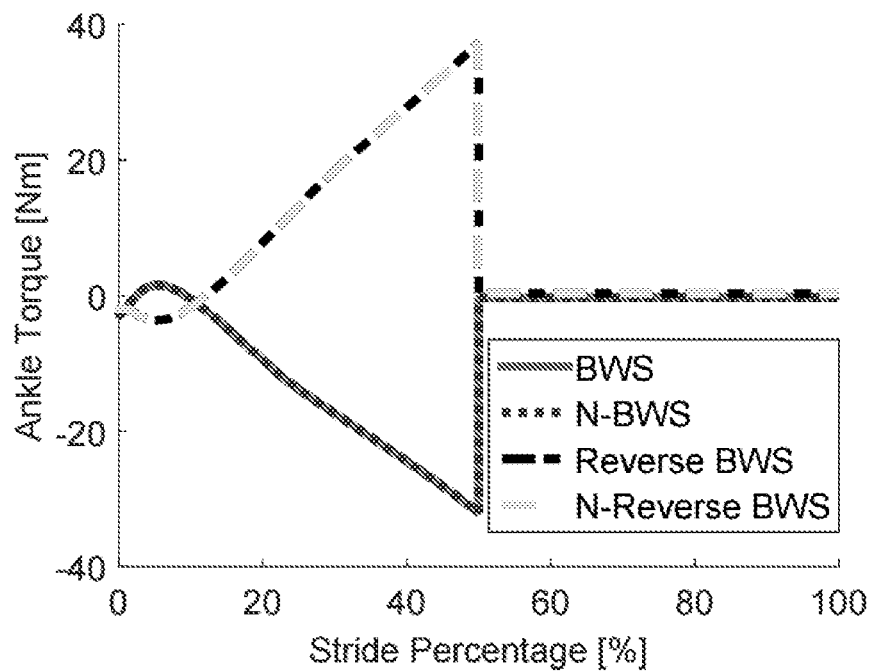
FIG. 4 illustrates a graph of torque profiles of a controller for the embodiment of FIG. 1.

For notational purposes, 35% BWS corresponds to $\tilde{g} = 0.65 \cdot g$, whereas 35% reverse BWS corresponds to $\tilde{g} = 1.35 \cdot g$. The torque profiles for these conditions are shown in FIG. 4. A peak torque of about 40 Nm is adopted as a design reference for the embodiment shown and described in FIG. 1, though smaller BWS percentages would require smaller torques. The simulations also show that the BWS condition performs negative work on the biped (by removing potential energy), whereas the opposite holds for reverse BWS.

Because the simulations in [13] show that the flat-foot controller $u_{flat}$ is equivalent to the other stance phase controllers ($u_{heel}$ and $u_{toe}$), the investigators also performed a simulation using $u_{flat}$ during all of stance. Given the similar behavior in FIG. 4, the investigators adopt $u_{flat}$ during stance for the experimental implementation disclosed herein to avoid practical difficulties in distinguishing between stance contact phases.

Actuator Control System Testing

Experimental Results

Figure 7:
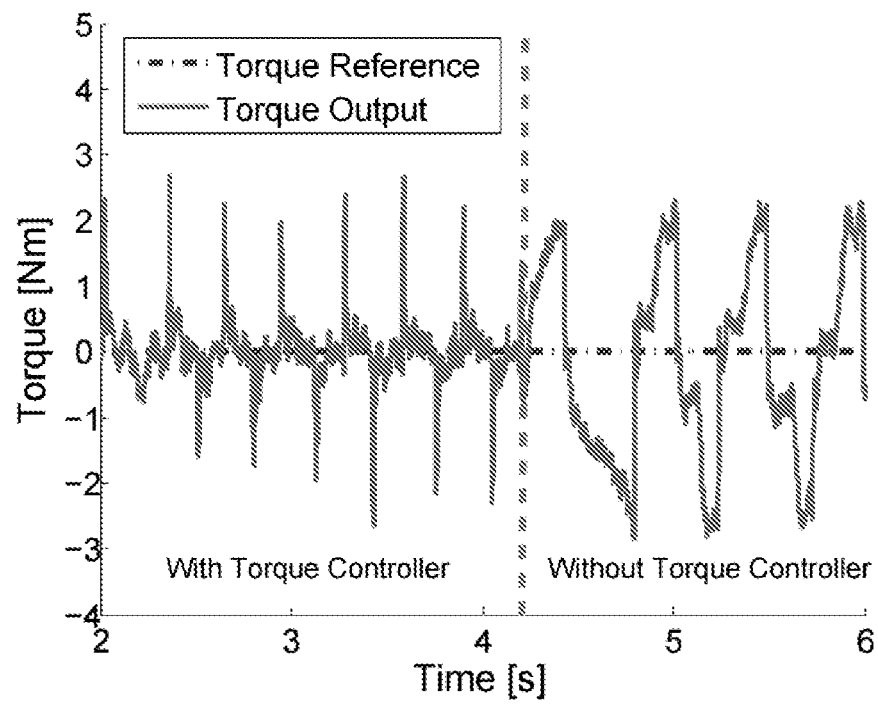
FIG. 7 illustrates a graph torque versus time for an actuator control system of the embodiment of FIG. 1.

Due to the fact that the magnitude of the backdrive torque could be greater than the reference torque during swing, the user would feel resistance at the ankle during swing. Therefore, the backdrive torque should be compensated by the closed torque control loop to make the PAFO more transparent to the user. The investigators conducted an experiment to verify the effects of backdrive torque compensation, where they put the PAFO on a fixed frame and moved the ankle joint manually to mimic ankle motion. The experimental results are shown in FIG. 7, where the torque reference was set to zero and we switched off the torque controller after 4.2 s. The standard deviation of the backdrive torque was reduced by 65%, from 1.47 Nm to 0.50 Nm, and the mean value was reduced to −0.05 Nm.

Figure 8:
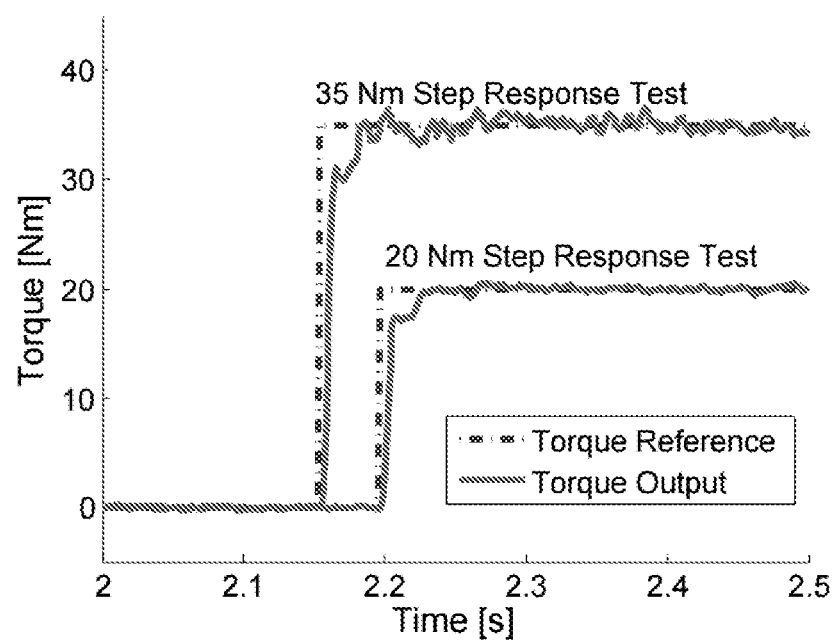
FIG. 8 illustrates a graph of Step response tracking test of the actuator control system of the embodiment of FIG. 1.

An experiment was also conducted to test the performance of torque tracking, where two reference torques, i.e., a 20 Nm step signal and a 35 Nm step signal, were given to approximate the situation when 20% or higher percentages of BWS are applied. Based on the results shown in FIG. 8, torque tracking was achieved for both experiments with steady error less than 4.5% of their torque references, respectively. These experiments validate the torque tracking loop for implementing the potential energy shaping strategy. The investigators are unaware of any prior PAFO design that can achieve such high torque and power with such low backdrive torque.

Figure 9:
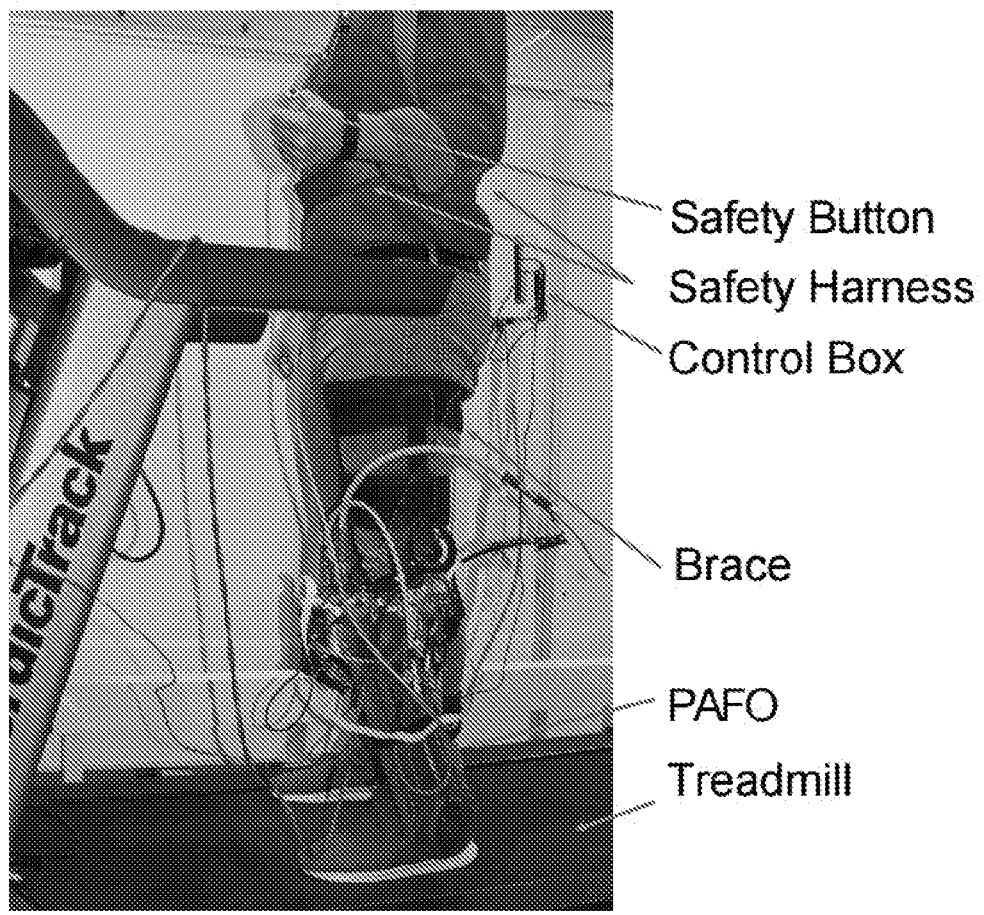
FIG. 9 illustrates a person testing the embodiment of FIG. 1.

The investigators experimentally tested the control algorithm on an adult male subject walking with the PAFO on a treadmill, where the experiment setup is shown in FIG. 9. For suspension the PAFO was attached to a knee brace, and the user's fit was tightened with straps. The control box worn on the subject's back contains the myRIO controller and two PCB boards for signal integration. The parameters used in the experiment are given in Table I below. The mass/inertia terms of the human subject were estimated from anatomical measurements and normalized data in [23], and the mass/inertia terms of the PAFO were calculated in SolidWorks.

TABLE 1

EXPERIMENTAL PARAMETERS

| Parameter | Variable | Value |
| --- | --- | --- |
| Subject Hip mass | $m_h$ | 34.8 [kg] |
| Subject Thigh mass | $m_t$ | 7 [kg] |
| Subject Shank mass | $m_s$ | 2.985 [kg] |
| Subject Foot mass | $m_f$ | 1.015 [kg] |
| Subject Thigh moment of inertia | $I_t$ | 0.1517 [kg · m$^2$] |
| Subject Shank moment of inertia | $I_s$ | 0.0653 [kg · m$^2$] |
| Subject shank length | $l_s$ | 0.458 [m] |
| Subject thigh length | $l_t$ | 0.4557 [m] |
| Subject heel length | $l_a$ | 0.073 [m] |
| Full biped foot length | $l_f$ | 0.275 [m] |
| PAFO Shank mass | $m_{so}$ | 2.998 [kg] |
| PAFO Foot mass | $m_{fo}$ | 0.27 [kg] |
| PAFO Shank moment of inertia | $I_{so}$ | 0.0603 [kg · m$^2$] |

A safety harness was attached to the subject's torso to minimize the risk of falling. The subject was initially given time to find a natural gait with the unpowered exoskeleton on the treadmill. The subject was told not to use the handrails of the treadmill unless balance was lost. Once the subject started walking naturally with the orthosis, the investigators started the experiments and recorded data.

For this initial validation study the investigators conducted two experiments with limited weight augmentation: 20% BWS and 10% reverse BWS. The investigators stopped at 10% reverse BWS because the subject was already struggling to walk with that amount of weight addition. At the beginning of each experiment, the investigators asked the subject to stand straight to initialize the feedback of the PAFO. Then, the subject started walking on the treadmill at a constant speed of 0.536 m/s while holding the safety button to keep the PAFO system powered. The investigators recorded data for 15 steps for each condition once steady walking was observed. After the data was collected, the BWS condition was changed and the investigators ran the experiment again.

Figure 10:
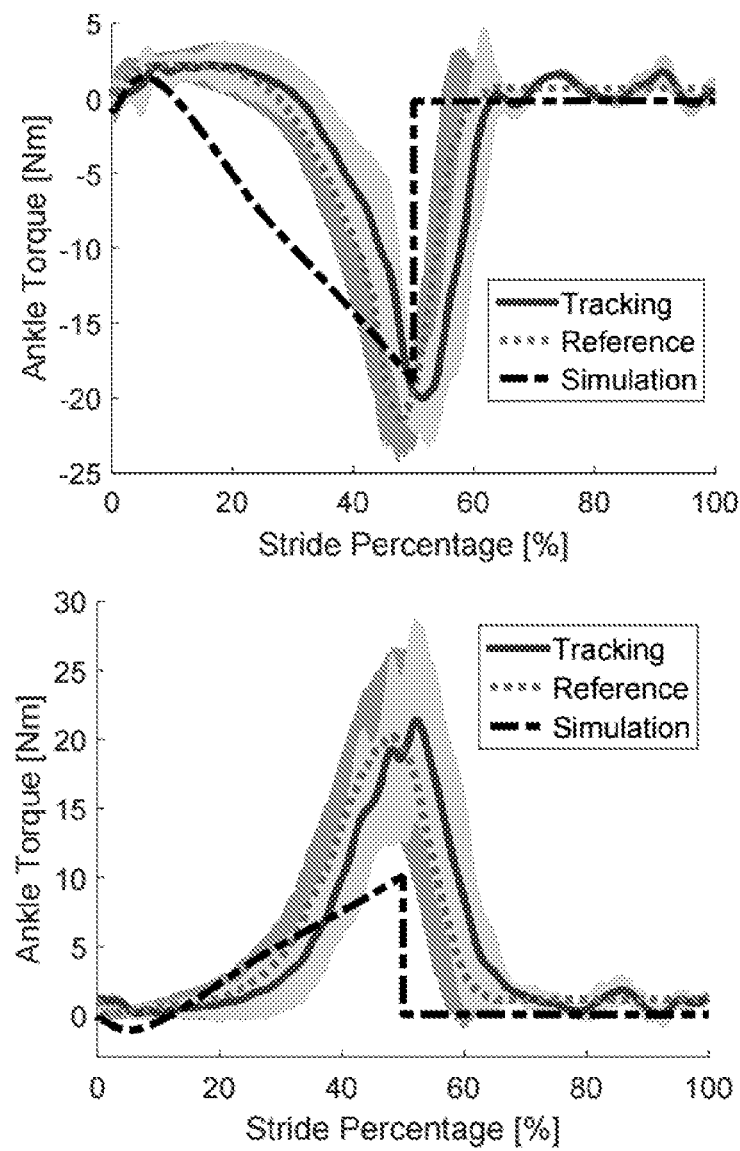
FIG. 10 illustrates graphs of torque versus stride percentage measuring during the testing illustrated in FIG. 9.

The experimental results for 20% BWS and 10% reverse BWS are shown in FIG. 10. Each curve (except the simulation torque) was calculated by taking the average of 15 steady steps, and the shaded regions represent ±1 standard deviation about the mean. Note that in the simulation the investigators assumed the biped model does not have a continuous double-support phase, i.e., only one leg is contacting the ground at all times, whereas human locomotion has a non-trivial double-support period. Hence, from the simulation torque the investigators can see the biped entered swing at 50% of the gait cycle, while in the conducted experiments, the swing controller took over at about 62% of the gait cycle (approximately the beginning of swing phase during human locomotion [23]). Since the magnitude of torque at toe contact was much higher than the magnitude at initial swing, the investigators applied a "fading process" throughout the double support phase, where the investigators took the weighted sum of the stance and swing torques to guarantee smooth and safe switching. For both experiments, backdrive torque was compensated by the actuator control system to minimize resistance for the subject, which can be observed in FIG. 10 during swing. The average mechanical work done by the PAFO per stride was −7.375 J and 4.942 J for the BWS and reverse BWS conditions, respectively, confirming the removal or addition of potential energy to the human subject.

From FIG. 10 one can see some differences between the peak torque of the simulation and experiments. This is reasonable since the simulation utilized average parameter values of adult males, which differ from the parameters of our subject in the experiments. The investigators also neglected the mass of the orthosis in the simulation, whereas the physical weight of the orthosis was modeled in the experimental controller, resulting in extra torques to compensate for this weight. There were small delays between the reference torques and the tracking torques, which might be caused by the torque PI controller shown in FIG. 5. The investigators manually tuned the PI controller gains in such a way that torque ripple and steady state error could be minimized, but with some sacrifice on response speed. However, these delays are acceptable for the slow walking considered here and in gait rehabilitation.

The estimated mass parameters in Table I did not need to be accurate, since the BWS percentage could be adjusted easily in the program based on the preference of the subject. The controller did not require velocity feedback, and precise contact measurement was not needed. These experiments therefore demonstrate that the potential energy shaping control strategy can be implemented with relative ease. For both experiments, the subject was able to walk safely and comfortably with both positive and negative weight augmentation, motivating future studies with additional human subjects, including patients, to understand the effects of this weight augmentation.

Figure 11:
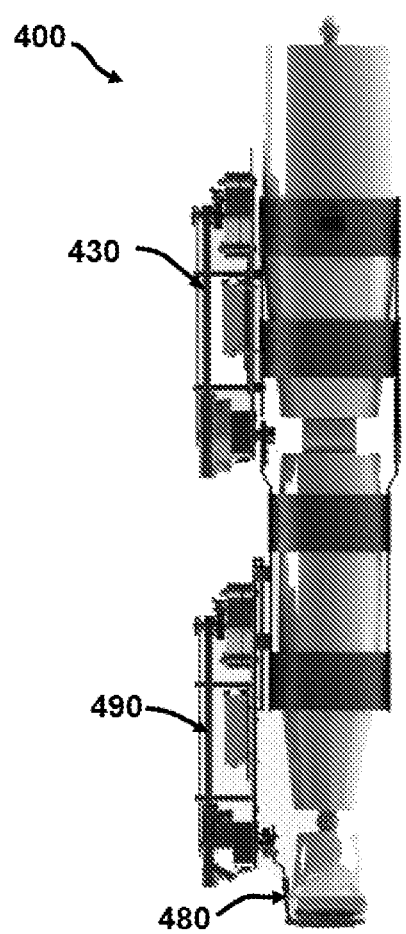
FIG. 11 illustrates a front view of a knee and ankle orthosis according to exemplary embodiments of the present disclosure.

Referring now to FIG. 11, an embodiment of an orthosis device 400 similar to that of previously-described embodiments is shown in a front view. Device 400 is shown worn by a person in a side view in FIG. 12. In this embodiment, device 400 comprises a knee actuator 431 coupled to an upper support member 430 and an ankle actuator 490 coupled to an intermediate support member 450. In addition, device 400 comprises a lower support member 480 coupled to ankle actuator 490 and configured for coupling to a user's foot (e.g. proximal to an insole in the user's shoe). A partial section view of knee actuator 430 is shown in FIG. 13.

Figure 13:
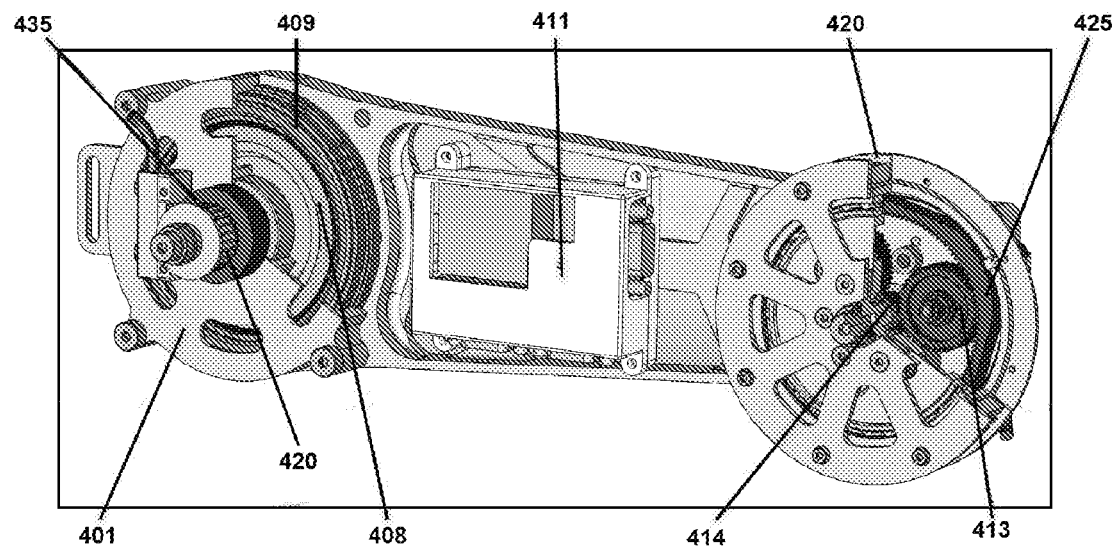
FIG. 13 illustrates a partial section view of the knee actuator of FIG. 11.

The embodiment shown in FIG. 13, knee actuator 431 comprises a motor 410 and a gearbox 412. In the embodiment shown, motor 410 may be configured as a permanent magnetic synchronous motor (PMSM). In this embodiment, motor 401 comprises a stator 409 and a rotor 408, while gearbox 412 is shown with a sun gear 414, planetary gear 413 and ring gear 415. Knee actuator 431 also comprises an encoder 435 and a driver sprocket 420, which may be coupled to driven sprocket 425 via a belt (not shown) in this embodiment. Knee actuator 431 also comprises an actuator driver or controller 411 configured to control motor 410. During operation, controller 411 can control the position or torque of motor 410, which in turn can control the position or torque of intermediate support member 450 to drive the position of the user's knee (via the drive belt and gearbox 412). Intermediate support member 450 is also coupled to ankle actuator 490, which drives the position of the user's ankle.

Figure 12:
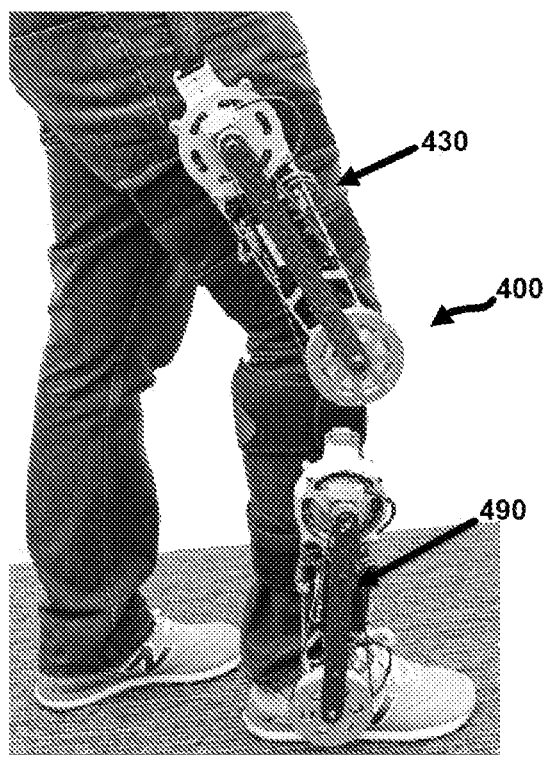
FIG. 12 illustrates a side view of the embodiment of FIG. 11 worn by a user.
Figure 14:
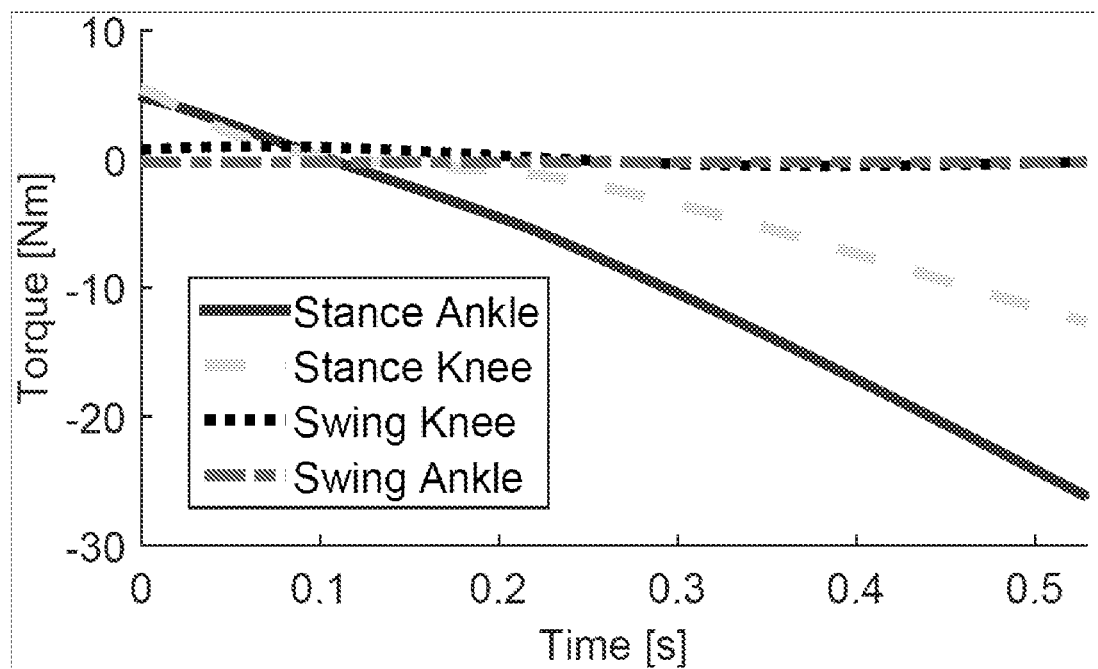
FIGS. 14 and 15 illustrate plots of simulated torques from the control system of the embodiment of FIGS. 11 and 12.
Figure 15:
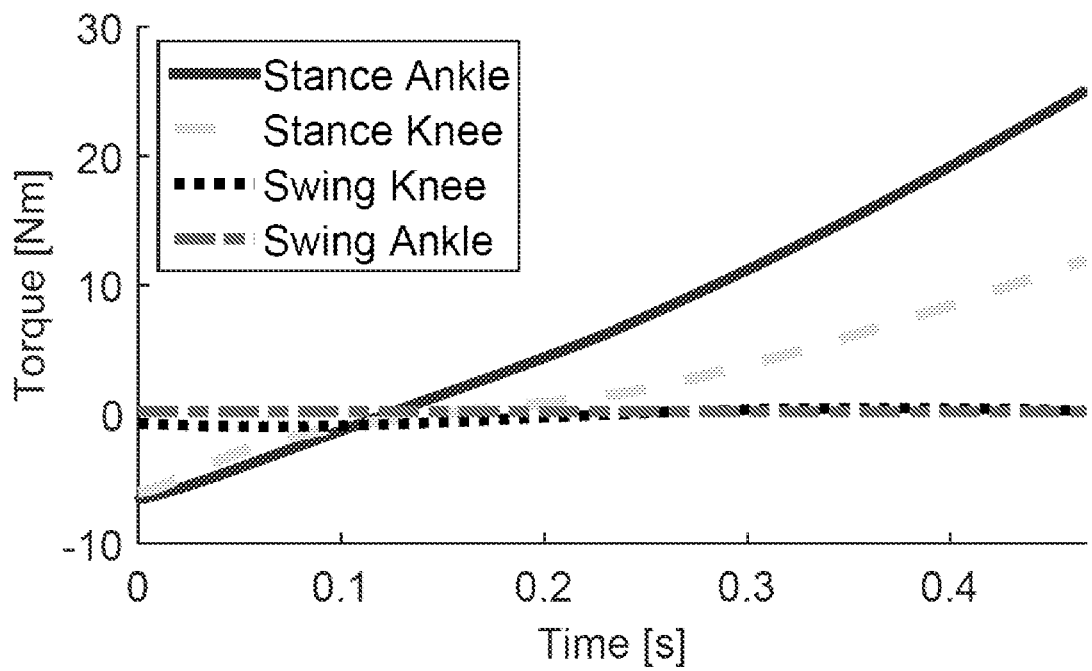

Referring now to FIGS. 14 and 15, plots of simulated torques from the control system are shown for device 400 (shown in FIGS. 11 and 12). The plots of FIGS. 14 and 15 illustrate providing 24.5% body-weight support vs. negative 24.5% body-weight support (i.e., adding weight) over an average walking step. The simulation model used to produce the plots in FIGS. 14 and 15 is similar to that shown in in FIGS. 2 and 3, but uses a powered knee-and-ankle orthosis rather than just a powered ankle orthosis.

In summary, the devices and methods disclosed herein present an implementation of potential energy shaping for torque control on a powered ankle-foot orthosis. Exemplary embodiments include a potential energy shaping controller for the ankle actuator derived and simulated on a biped model. Based on the simulation results, a highly backdrivable powered ankle-foot orthosis can be used to implement and test this torque control strategy for a clinically relevant orthosis for persons including, for example, stroke patients. Initial experiments demonstrate that the disclosed PAFO control system can track the reference torque generated by the high-level control.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

[1] T. Yan, M. Cempini, C. M. Oddo, and N. Vitiello, "Review of assistive strategies in powered lower-limb orthoses and exoskeletons," Robotics and Autonomous Systems, vol. 64, pp. 120-136, 2015.

[2] R. J. Farris, H. Quintero, and M. Goldfarb, "Preliminary evaluation of a powered lower limb orthosis to aid walking in paraplegic individuals," Neural Systems and Rehabilitation Engineering, IEEE Transactions on, vol. 19, no. 6, pp. 652-659, 2011.

[3] K. A. Strausser and H. Kazerooni, "The development and testing of a human machine interface for a mobile medical exoskeleton," in IEEE Int. Conf. Intelligent Robots Systems. IEEE, 2011, pp. 4911-4916.

[4] A. Duschau-Wicke, T. Brunsch, L. Lunenburger, and R. Riener, "Adaptive support for patient-cooperative gait rehabilitation with the lokomat," in IEEE Int. Conf. Intelligent Robots Systems, 2008, pp. 2357-2361.

[5] D. Sanz-Merodio, M. Cestari, J. C. Arevalo, and E. Garcia, "A lowerlimb exoskeleton for gait assistance in quadriplegia," in Int. Conf Robotics and Biomimetics. IEEE, 2012, pp. 122-127.

[6] Y. Sankai, "Hal: Hybrid assistive limb based on cybernics," in Robotics Research. Springer, 2011, pp. 25-34.

[7] M. Talaty, A. Esquenazi, and J. E. Briceno, "Differentiating ability in users of the Rewalk™ powered exoskeleton: An analysis of walking kinematics," in IEEE Int. Conf. Rehabilitation Robotics, 2013.

[8] J. Hidler, D. Nichols, M. Pelliccio, K. Brady, D. D. Campbell, J. H. Kahn, and T. G. Hornby, "Multicenter randomized clinical trial evaluating the effectiveness of the lokomat in subacute stroke," Neurorehabilitation and Neural Repair, vol. 23, no. 1, pp. 5-13,2009.

[9] M. R. Tucker, J. Olivier, A. Pagel, H. Bleuler, M. Bouri, O. Lambercy, J. d. R. Millan, R. Riener, H. Vallery, and R. Gassert, "Control strategies for active lower extremity prosthetics and orthotics: a review," J. of neuroengineering and rehabilitation, vol. 12, no. 1, p. 1,2015.

[10] J. Ghan, R. Steger, and H. Kazerooni, "Control and system identification for the berkeley lower extremity exoskeleton (BLEEX)," Advanced Robotics, vol. 20, no. 9, pp. 989-1014, 2006.

[11] G. Blankenstein, R. Ortega, and A. J. Van Der Schaft, "The matching conditions of controlled lagrangians and ida-passivity based control," International Journal of Control, vol. 75, no. 9, pp. 645-665, 2002.

[12] G. Lv and R. D. Gregg, "Orthotic body-weight support through underactuated potential energy shaping with contact constraints," in Decision and Control, 2015 54th IEEE Conference on. IEEE, 2015.

[13] G. Lv and R. D. Gregg, "Underactuated potential energy shaping with contact constraints: Application to a powered knee-ankle orthosis," Control Systems Techonology, IEEE Transactions on, 2017, in press.

[14] R. D. Gregg, T. Lenzi, L. J. Hargrove, and J. W. Sensinger, "Virtual Constraint Control of a Powered Prosthetic Leg: From Simulation to Experiments with Transfemoral Amputees." Robotics, IEEE Transactions on, vol. 30, no. 6, pp. 1455-1471, December 2014.

[15] R. M. Murray, Z. Li, S. S. Sastry, and S. S. Sastry, A Mathematical Introduction to Robotic Manipulation. CRC press, 1994.

[16] R. D. Gregg and J. W. Sensinger, "Biomimetic virtual constraint control of a transfemoral powered prosthetic leg," in American Control Conference. IEEE, 2013, pp. 5702-5708.

[17] E. R. Westervelt, J. W. Grizzle, and D. E. Koditschek, "Hybrid zero dynamics of planar biped walkers," Automatic Control, IEEE Transactions on, vol. 48, no. 1, pp. 42-56, 2003.

[18] P. De Leva, "Adjustments to zatsiorsky-seluyanov's segment inertia parameters," J. Biomechanics, vol. 29, no. 9, pp. 1223-1230, 1996.

[19] R. L. Waters and S. Mulroy, "The energy expenditure of normal and pathologic gait," Gait & posture, vol. 9, no. 3, pp. 207-231, 1999.
[20] T. M. Jahns and W. L. Soong, "Pulsating torque minimization techniques for permanent magnet ac motor drives-a review," Industrial Electronics, IEEE Transactions on, vol. 43, no. 2, pp. 321-330, 1996.
[21] J. P. John, S. S. Kumar, and B. Jaya, "Space vector modulation based field oriented control scheme for brushless dc motors," in IEEE Int. Conf. Emerging Trends Electrical Computer Tech., 2011, pp. 346-351.
[22] E. Oksurtepe, Z. Omac, and H. Kurum, "Sensorless vector control of pmsm with non-sinusoidal flux using observer based on fem," Electrical Engineering, vol. 96, no. 3, pp. 227-238, 2014.
[23] D. A. Winter, Biomechanics and Motor Control of Human Movement. John Wiley & Sons, 2009.

The invention claimed is:

1. A method for controlling an orthosis device coupled to a leg of a person, the method comprising:
    measuring forces exerted on the orthosis device, wherein the orthosis device comprises an actuator, a plurality of support members and a plurality of sensors, and wherein the forces include a gravitational force exerted on the person;
    applying a torque to one of the plurality of support members by the actuator; and
    controlling the torque applied by the actuator, wherein:
        the leg to which the orthosis device is coupled of the person is modeled as a first kinematic chain when the leg to which the orthosis device is coupled of the person is in a stance phase;
        the leg to which the orthosis device is coupled of the person is modeled as a second kinematic chain when the leg to which the orthosis device is coupled of the person is in a swing phase;
        the gravitational force exerted on the person is estimated through models of the first and second kinematic chains;
        the torque applied by the actuator is controlled to counteract the gravitational force exerted on the person estimated through models of the first and second kinematic chains;
        the torque applied by the actuator is not controlled to direct the orthosis device in a pre-determined pattern of motion;
        the torque applied by the actuator is controlled by a control system;
        the control system shapes a closed-loop potential energy of the person;
        the closed-loop potential energy of the person has modified mass parameters or modified gravity parameters;
        the torque applied by the actuator is kinetically controlled via a nonlinear control method; and
        the torque is calculated using a kinematic model of only the leg to which the orthosis device is coupled, wherein the kinematic model depends on the coordinates of the leg to which the orthosis device is coupled.

2. The method of claim 1 wherein controlling the torque to the actuator comprises varying the current to an electric motor.

3. The method of claim 2 wherein the electric motor is a permanent magnetic synchronous motor.

4. The method of claim 1 wherein:
    the orthosis device comprises a first support member placed under a foot of the person;
    the orthosis device comprises a second support member coupled to a shin of the person; and
    the actuator is configured to vary the angle between the first support member and the second support member.

5. The method of claim 4 wherein measuring forces exerted on the orthosis device with the plurality of sensors comprises measuring a force in a ball area of the foot of the person via a first sensor in the first support member.

6. The method of claim 4 wherein measuring forces exerted on the orthosis device with a plurality of sensors comprises measuring a force in a heel area of the foot of the person via a second sensor in the first support member.

7. The method of claim 4 wherein:
    the actuator comprises an electric motor coupled to a gearbox and a first sprocket;
    the orthosis device comprises a second sprocket coupled to the first support member; and
    the orthosis device comprises a belt coupling the first sprocket and the second sprocket.

8. The method of claim 7 further comprising measuring the torque applied to one of the plurality of support members by the actuator with a reaction torque sensor.

9. The method of claim 8 wherein the gearbox comprises a planetary gear transmission, and wherein the reaction torque sensor measures the torque at an end of the planetary gear transmission.

10. The method of claim 4 further comprising measuring an angle of the second support member via an inertial measurement unit.

11. An orthosis device comprising:
    a first support member configured to be coupled to a leg of a person;
    a second support member configured to be coupled to the leg to which the first support member is coupled of the person;
    a plurality of sensors configured to measure forces exerted on the orthosis device, wherein the forces exerted on the orthosis device include a gravitational force;
    an actuator configured to apply a torque to the first or second support member; and
    a controller configured to control the torque applied by the actuator, wherein:
        the leg to which the first support member and the second support member are coupled of the person is modeled as a first kinematic chain when the leg to which the first support member and the second support member are coupled of the person is in a stance phase;
        the leg to which the first support member and the second support member are coupled of the person is modeled as a second kinematic chain when the leg to which the first support member and the second support member are coupled of the person is in a swing phase;
        the gravitational force exerted on the orthosis device is estimated through models of the first and second kinematic chains;
        the torque is controlled to counteract the gravitational force exerted on the orthosis device estimated through models of the first and second kinematic chains and wherein the torque is not controlled to direct the orthosis device in a pre-determined pattern of motion;
        the controller comprises a control system;
        the control system is configured to shape a closed-loop potential energy of the person and the orthosis device;

the closed-loop potential energy of the person and the orthosis device has modified mass parameters or modified gravity parameters;

the torque applied by the actuator is kinetically controlled via a nonlinear control method; and the torque is calculated using a kinematic model of only the leg to which the orthosis device is coupled, wherein the kinematic model depends on the coordinates of the leg to which the orthosis device is coupled.

12. The orthosis device of claim 11 wherein the actuator comprises an electric motor, and wherein the controller is configured to vary the current to the electric motor.

13. The orthosis device of claim 11 wherein:

the first support member is configured to be placed under a foot of a person;

the second support member is configured to be coupled to a shin of a person; and the actuator is configured to vary the angle between the first support member and the second support member.

14. The orthosis device of claim 13 wherein the plurality of sensors comprises a first sensor in the first support member configured to measure a force in a ball area of the foot of the person.

15. The orthosis device of claim 13 wherein the plurality of sensors comprises a second sensor in the first support member configured to measure a force in a heel area of the foot of the person.

16. The orthosis device of claim 13 further comprising an inertial measurement unit configured to measure an angle of the second support member.

17. The orthosis device of claim 11 further comprising an optical encoder configured to measure an angle between the first support member and the second support member.

18. The orthosis device of claim 11 wherein:

the actuator comprises an electric motor coupled to a gearbox and a first sprocket;

the orthosis device comprises a second sprocket coupled to the first support member; and the orthosis device comprises a belt coupling the first sprocket and the second sprocket.

19. The orthosis device of claim 18 further comprising a reaction torque sensor coupled to the gearbox.

20. The orthosis device of claim 19 wherein the gearbox comprises a planetary gear transmission, and wherein the reaction torque sensor is configured to measure torque at an end of the planetary gear transmission.

* * * * *